US012582514B2

(12) United States Patent     (10) Patent No.:    US 12,582,514 B2

Ketonis        (45) Date of Patent:     Mar. 24, 2026

(54) TENDON REPAIR IMPLANT AND SURGICAL INSTRUMENTS FOR TENDON REPAIR

(71) Applicant: Ketonis Innovations LLC, Webster, NY (US)

(72) Inventor: Constantinos Ketonis, Webster, NY (US)

(73) Assignee: Ketonis Innovations LLC, Webster, NY (US)

( * ) Notice: Subject to any disclaimer, the term of this patent is extended or adjusted under 35 U.S.C. 154(b) by 764 days.

(21) Appl. No.: 17/275,477

(22) PCT Filed: Sep. 11, 2019

(86) PCT No.: PCT/US2019/050702

§ 371 (c)(1),
(2) Date: Mar. 11, 2021

(87) PCT Pub. No.: WO2020/056063

PCT Pub. Date: Mar. 19, 2020

(65) Prior Publication Data

US 2022/0039942 A1     Feb. 10, 2022

Related U.S. Application Data

(60) Provisional application No. 62/731,789, filed on Sep. 14, 2018.

(51) Int. Cl.
A61F 2/08        (2006.01)

(52) U.S. Cl.
CPC .......... A61F 2/0811 (2013.01); A61F 2/0805 (2013.01); *A61F 2002/0817* (2013.01);
(Continued)

(58) Field of Classification Search
CPC ..... A61B 17/0642; A61B 17/84; A61B 17/90; A61B 17/8047; A61B 17/844;
(Continued)

(56) References Cited

U.S. PATENT DOCUMENTS 3,403,958 A * 10/1968 Gross ........................ G02C 5/22
                                       411/113
7,097,654 B1    8/2006   Freedland
(Continued)

FOREIGN PATENT DOCUMENTS

EP         3042622 A1 *   7/2016    ......... A61B 17/8076
WO    WO-9625892 A1 *   8/1996    ......... A61B 17/8047
(Continued)

OTHER PUBLICATIONS

International Preliminary Report on Patentability issued in PCT Application No. PCT/US2019/050702, dated Mar. 25, 2021, 9 pages.

(Continued)

*Primary Examiner* — Christie Bahena
(74) *Attorney, Agent, or Firm* — Heslin Rothenberg Farley & Mesiti P.C.

(57)            ABSTRACT

A tendon repair implant and related surgical instruments are disclosed. The tendon repair implant has an elongated substrate with a convex side and a concave side with a plurality of spikes protruding from the concave side at an angle that optimally retains a. tendon to the bone that the tendon repair implant is subsequently attached to. A surgical retainer for the tendon repair implant is also provided that releasably retains the tendon repair implant during surgery and implantation, A drill guide instrument for the tendon repair implant Is also provided that allows the surgeon to precisely place fastening holes in the bone prior to implantation of the tendon repair implant.

23 Claims, 20 Drawing Sheets

(52) U.S. Cl.
CPC ................. *A61F 2002/0858* (2013.01); *A61F 2002/0888* (2013.01); *A61F 2220/0016* (2013.01)

(58) Field of Classification Search
CPC ... A61B 17/8695; A61B 17/80; A61B 17/686; A61F 2/0811; A61F 2002/0817; A61F 2002/0823; A61F 2002/0835; A61F 2002/0847; A61F 2002/0858; A61F 2002/0864; A61F 2002/0888; A61F 2220/0016
USPC ......................................................... 411/21
See application file for complete search history.

(56) References Cited

U.S. PATENT DOCUMENTS

| | | | | |
|---|---|---|---|---|
| 8,951,293 | B2 * | 2/2015 | Glazer | ................. A61B 17/686 |
| | | | | 411/63 |
| 2003/0074021 | A1 | 4/2003 | Morriss et al. | |
| 2004/0260340 | A1 * | 12/2004 | Jacobs | ................... A61B 90/02 |
| | | | | 606/221 |
| 2009/0192551 | A1 * | 7/2009 | Cianfrani | ............. A61B 17/863 |
| | | | | 606/301 |
| 2010/0191332 | A1 | 7/2010 | Euteneuer et al. | |
| 2011/0004221 | A1 | 1/2011 | Euteneuer et al. | |
| 2011/0152930 | A1 * | 6/2011 | Howe | ................ A61B 17/0401 |
| | | | | 606/232 |
| 2013/0153628 | A1 | 6/2013 | Euteneuer et al. | |
| 2013/0245682 | A1 | 9/2013 | Euteneuer et al. | |
| 2017/0189164 | A1 | 7/2017 | Zenz-Olson et al. | |

FOREIGN PATENT DOCUMENTS

| | | | | |
|---|---|---|---|---|
| WO | | 2018035066 | A1 | 2/2018 |
| WO | WO-2018092129 | A1 * | 5/2018 | ......... A61B 17/0401 |

OTHER PUBLICATIONS

European Patent Office, International Search Report and Written Opinion for PCT App. No. PCT/US2019/050702 dated Dec. 11, 2019, 12 pages.

* cited by examiner

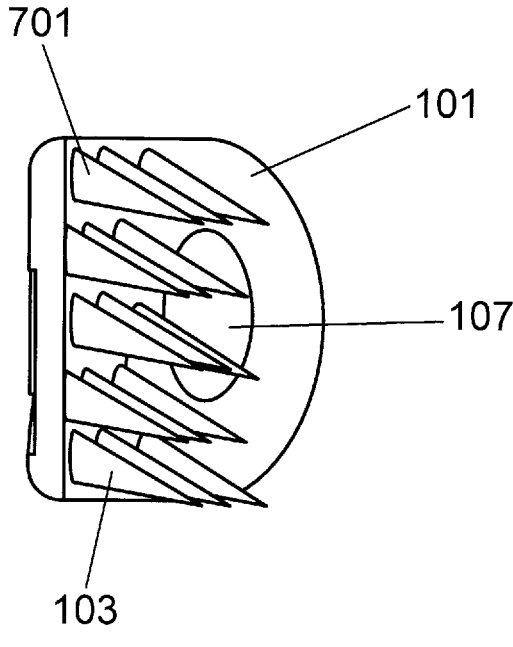
Fig. 7
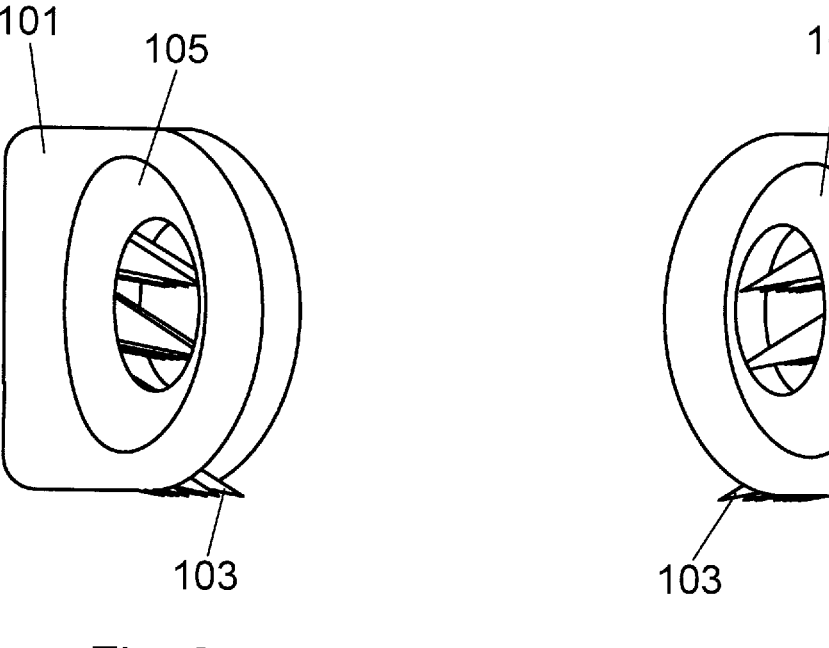
Fig. 8                              Fig. 9

TENDON REPAIR IMPLANT AND SURGICAL INSTRUMENTS FOR TENDON REPAIR

CROSS REFERENCE TO RELATED PATENT APPLICATIONS

This application claims priority to U.S. patent application Ser. No. 62/731,789 filed Sep. 14, 2018 entitled "Tendon Repair Implant And Surgical Instruments For Tendon Repair" by Constantinos Ketonis, the entire disclosure of which is incorporated herein by reference as permissible by national or regional laws.

TECHNICAL FIELD

The present invention relates generally to medical devices, and more particularly to a tendon repair implant and surgical instruments thereof.

BACKGROUND ART

Tendon avulsion injuries of the finger often impede proper anatomical functioning of the finger and hand, frequently leading to long term sequaele such as boutonniere's deformities, swan-neck deformities as well as mallet fingers. Such sequaele typically results in significant patient disability over time. Despite great advancements in medical technology, manufacturing processes and available biocompatible materials, little progress has been made in the way that we address these injuries of the finger and hand. The basic surgical corrective approach typically involves passing locking/grasping sutures through the avulsed or lacerated tendon edge with subsequent surgical re-approximation of the tendon edge to the bone, either through the use of bone tunnels, anchors or buttons.

Various combinations of the above surgical techniques have been described but no known technique has emerged as the optimal fixation technique for these tendon avulsion injuries.

During surgery, most strong locking suture configurations involve handling the tendon multiple times to prevent the suture from "cutting-through" when subjected to load. This process is not only time consuming during surgery but also leads to injury and fraying of the tendon. In addition, grasping sutures cannot span the whole width of the tendon, so when the tendon is brought down to bone during such surgical repair, it typically does not lay flat onto its insertion, but rather, ends up as a bulbous stump with limited bone-tendon interface or footprint, resulting in a prominent bulky repair.

For bone fixation of the tendon, one technique that has been used for a very long time is the button-over-nail technique using a surgical button and an affixing nail or screw. Unfortunately, this technique and the associated surgical button has been associated with numerous complications including nail deformities, fixed flexion deformities of the distal interphalangeal joint, infections and prolonged hypersensitivity. Alternatively, bone anchors have been used tor tendon reattach men t and repair, but depending on bone quality, their pull-out strength can be inadequate. Furthermore, in cases where the proximal aspect of a phalanx is comminuted, such as in cases of a middle phalanx pilon fracture with an associated central slip avulsion injury, there is no bony support for anchor placement and therefore surgical repair options are limited.

What is therefore needed is a surgical implant that aims to render tendon to bone repairs fast, reproducible, and robust while minimizing handling of the tendon during surgery and eliminating bulk at the repair site. Surgical instruments to facilitate the proper implantation of such a surgical implant are also needed and desirable.

DISCLOSURE OF THE INVENTION

In accordance with the present invention, there is provided a tendon repair implant comprising an elongated substrate having a convex side and a concave side; a plurality of spikes protruding from the concave side; wherein each spike protrudes from the concave side of the substrate at tin angle in the range of zero degrees to 45 degrees with respect to a line perpendicular to the concave surface of the substrate where the spike originates; a first attachment for fastening the substrate to a mammalian bone with the concave side of the substrate facing the mammalian bone; and a second attachment for fastening the substrate to a mammalian bone with the concave side of the substrate facing the mammalian bone. A surgical instrument for retaining and releasing the tendon repair implant during surgery and a surgical instrument that provides a drill guide and facilitates the correct placement of a bone attachment device (such as a surgical screw) for the tendon repair implant are also provided.

The foregoing paragraph has been provided by way of introduction, and is not intended to limit the scope of the invention as described by this specification, claims and the attached drawings.

BRIEF DESCRIPTION OF THE DRAWINGS

The invention will be described by reference to the following drawings, in which like numerals refer to like elements, and in which:

FIG. 7 is a cross sectional view of the tendon repair implant taken along line A-A of FIG. 4;

FIG. 8 is a first attachment end perspective view of the tendon repair implant;

FIG. 9 is a second attachment end perspective view of the tendon repair implant;

3

Figure 10:
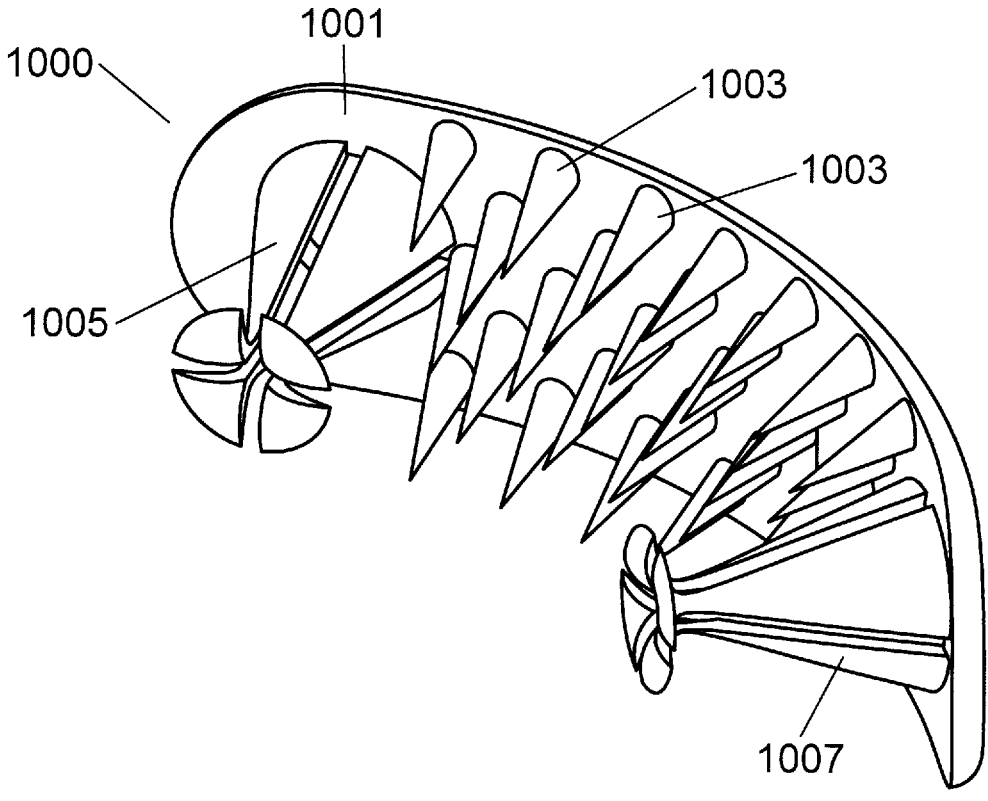
FIG. 10 depicts a perspective view of the tendon repair implant with attached bone attachment devices.
Figures 17, 18:
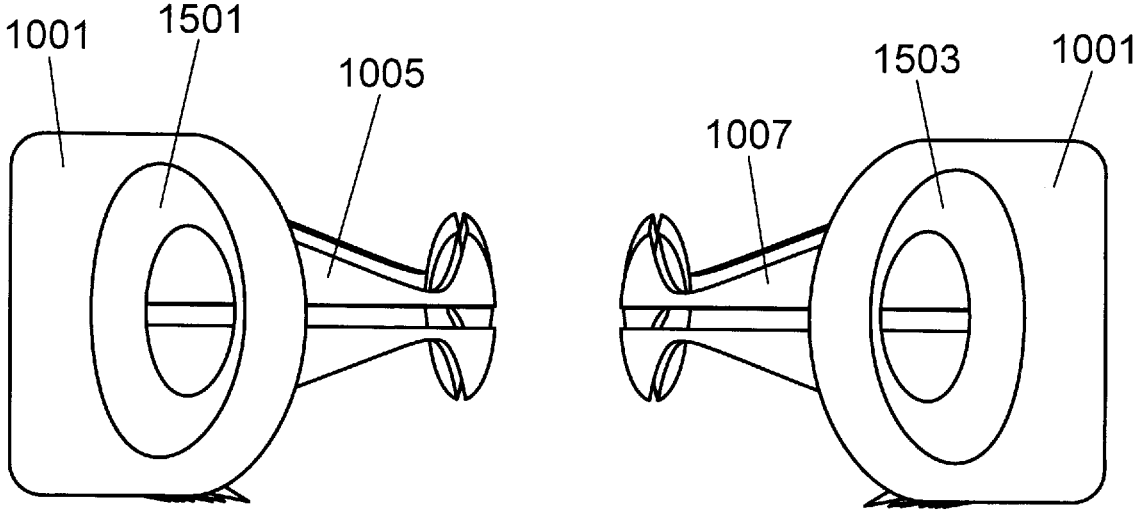
Figure 19:
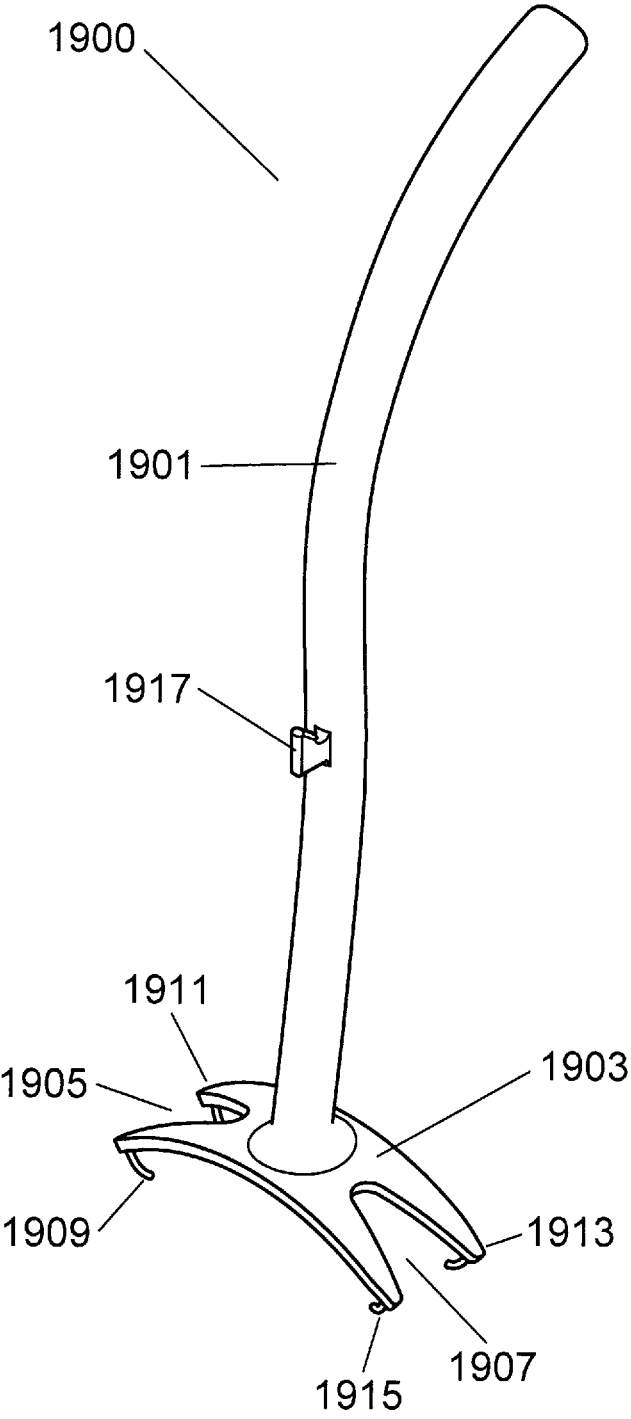
Figure 20:
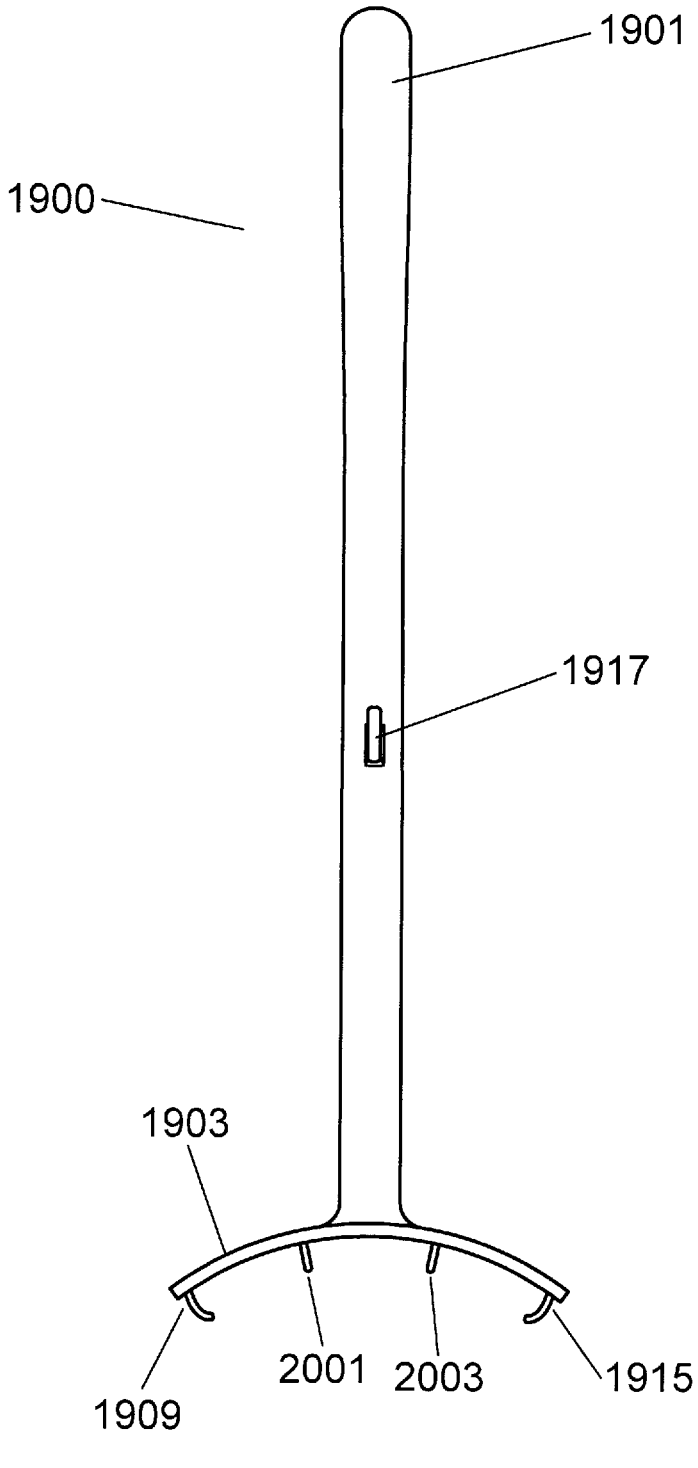
Figure 21:
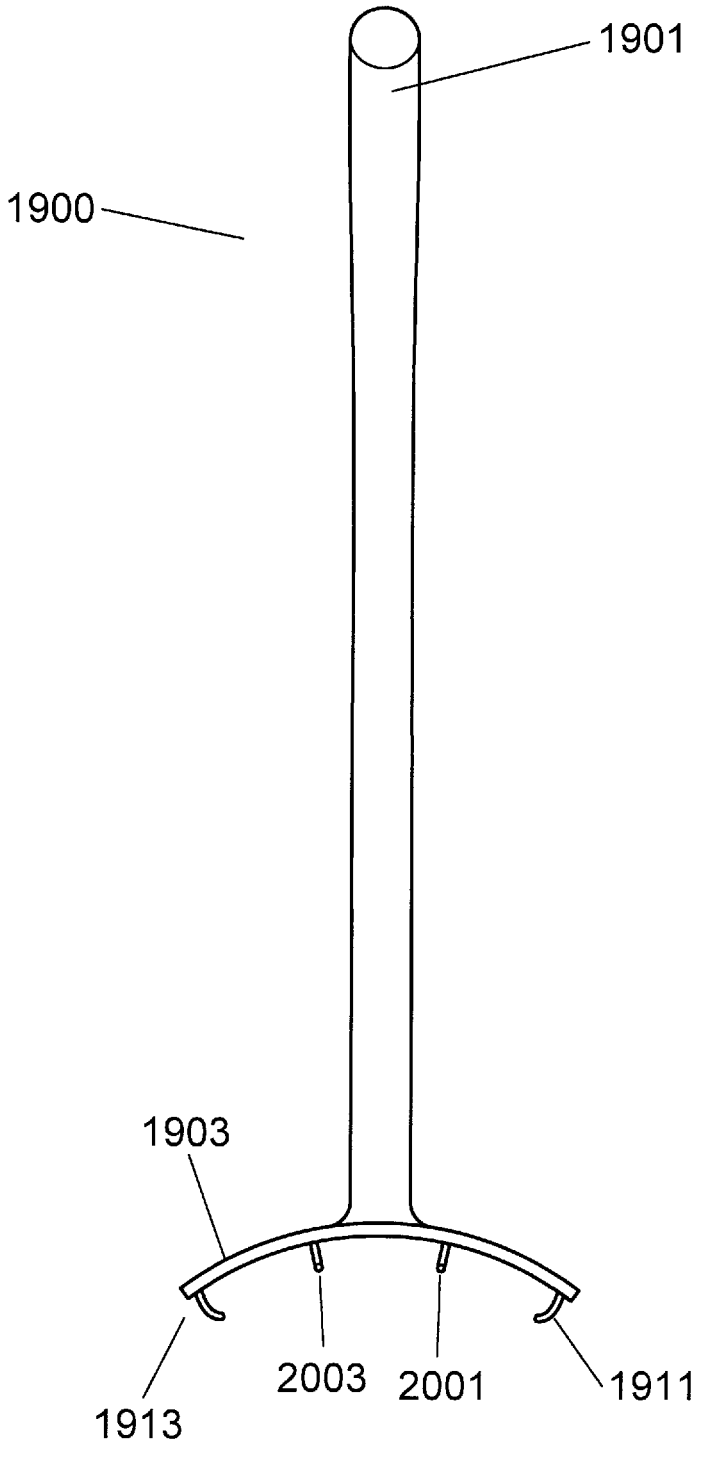
Figure 22:
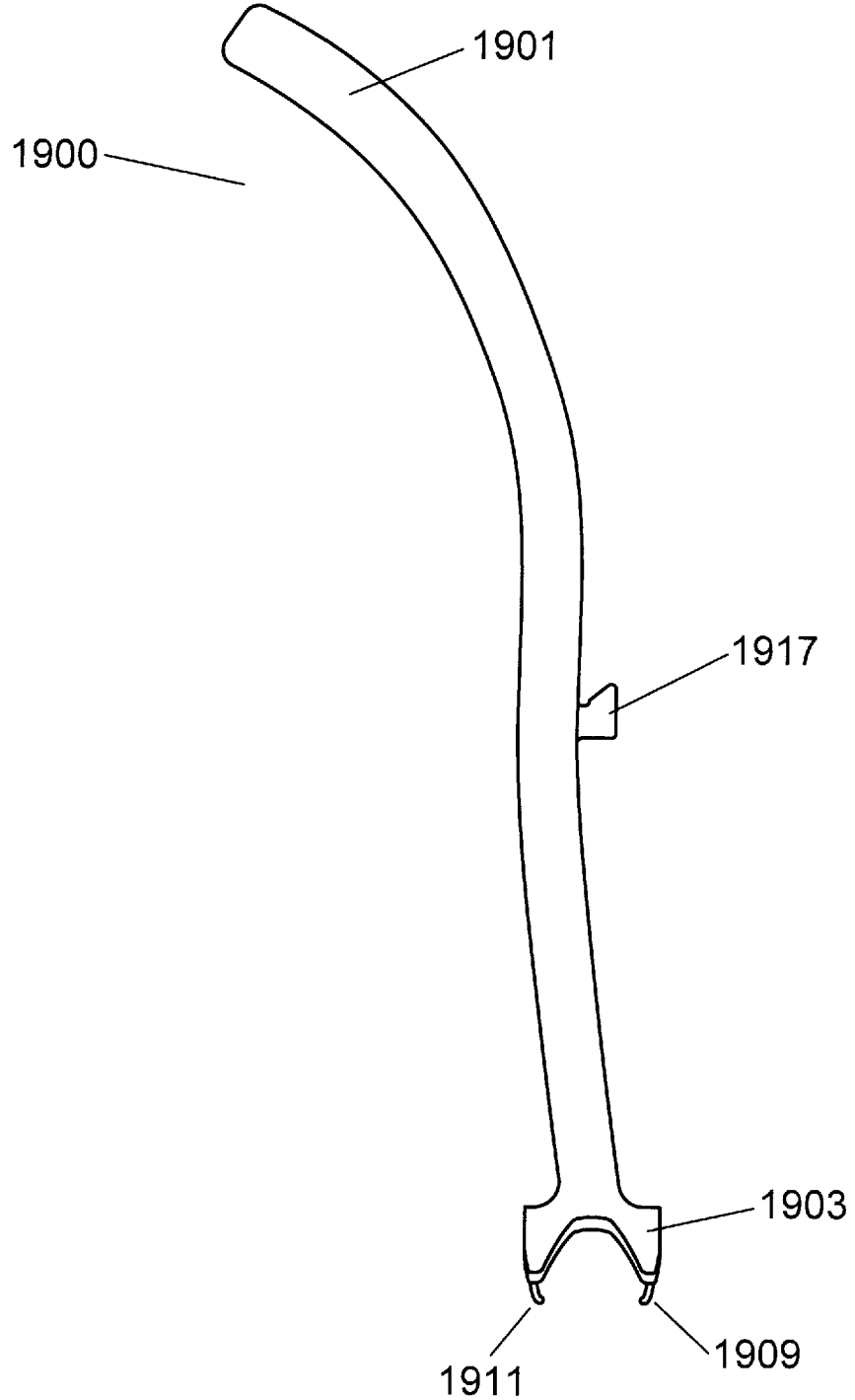
Figure 23:
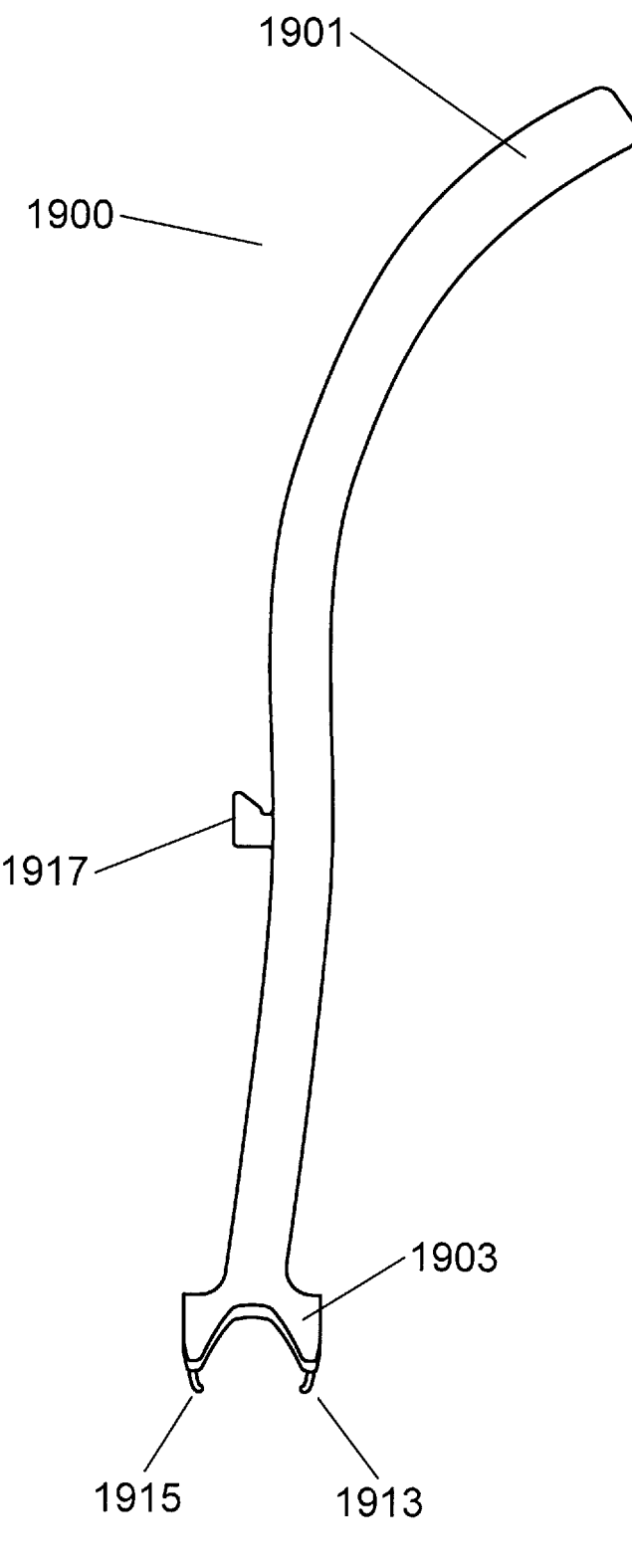
Figure 24:
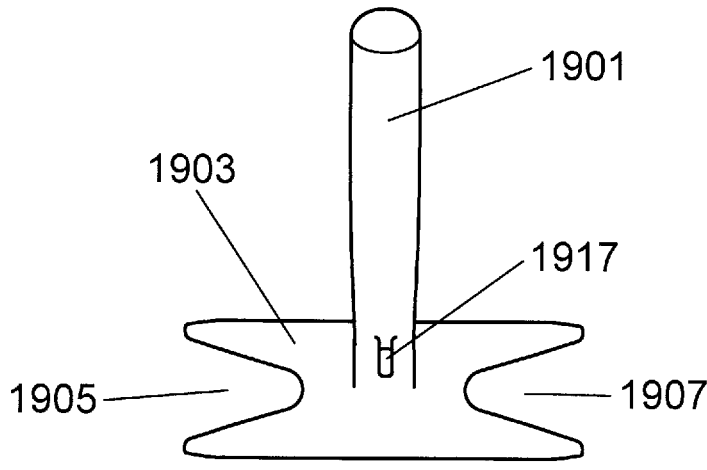
Figure 25:
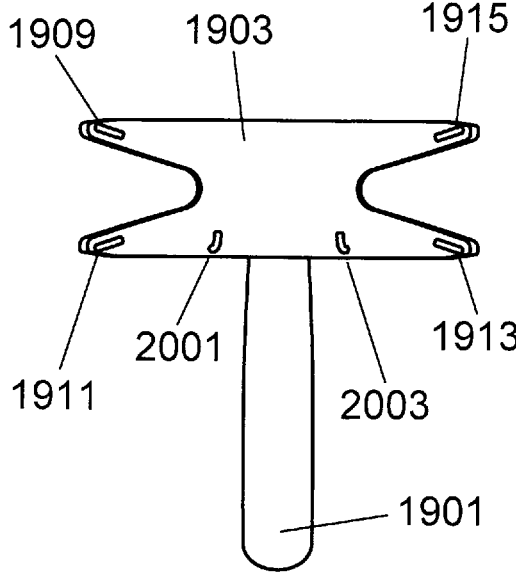
Figure 26:
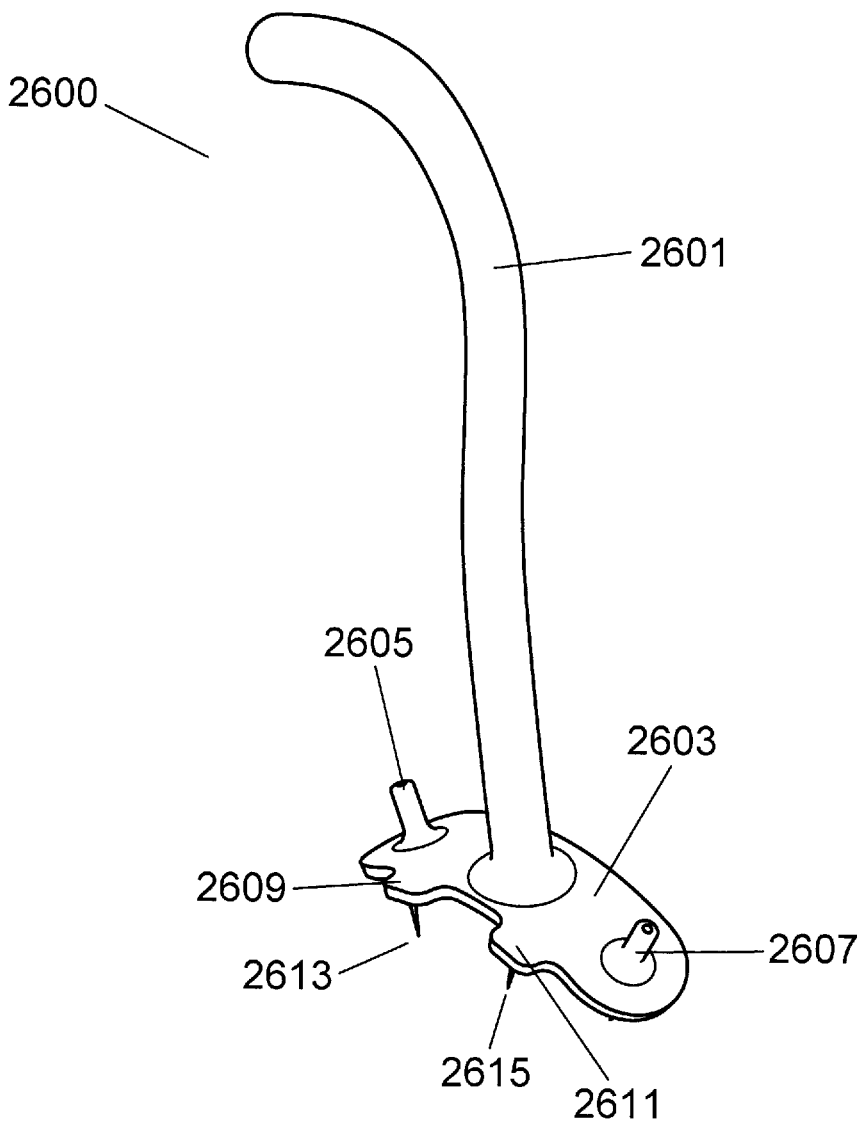
Figure 27:
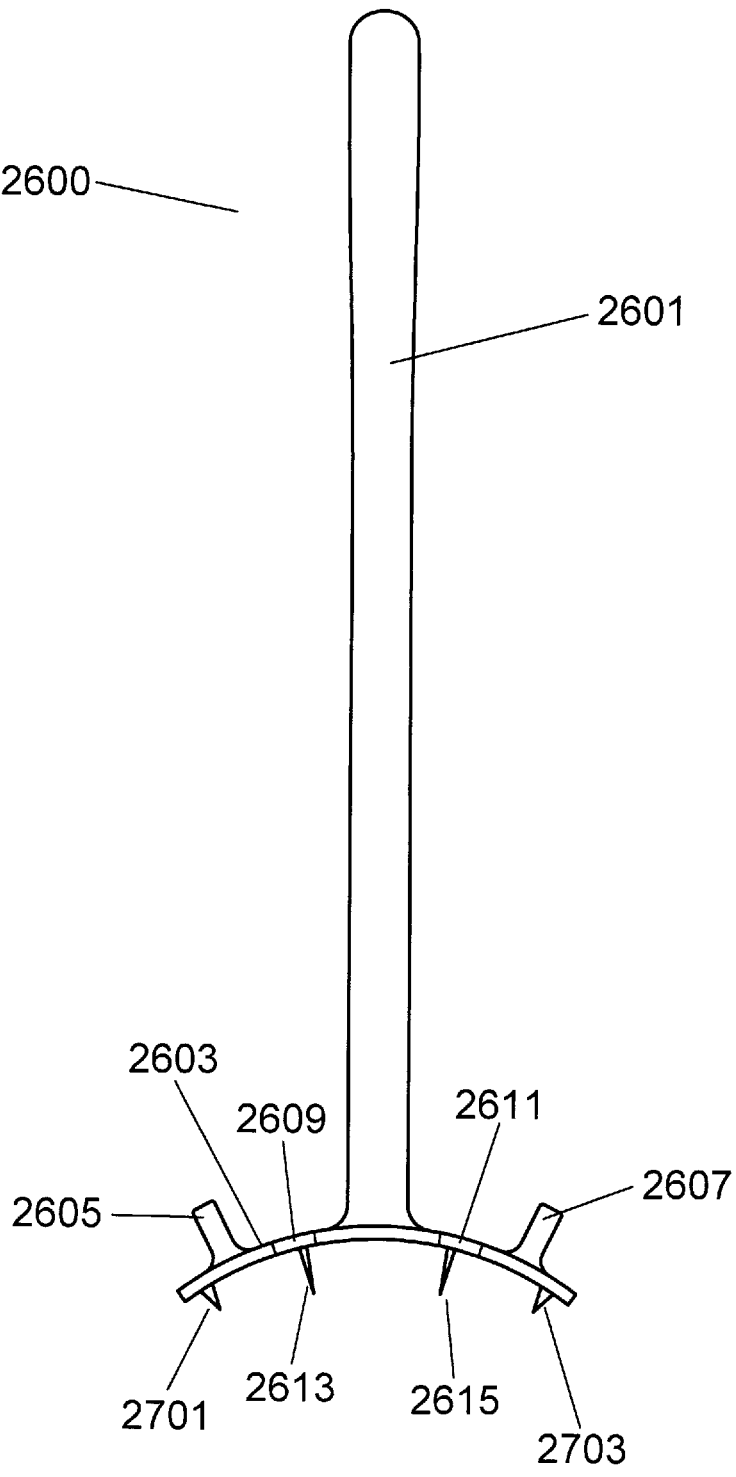
Figure 28:
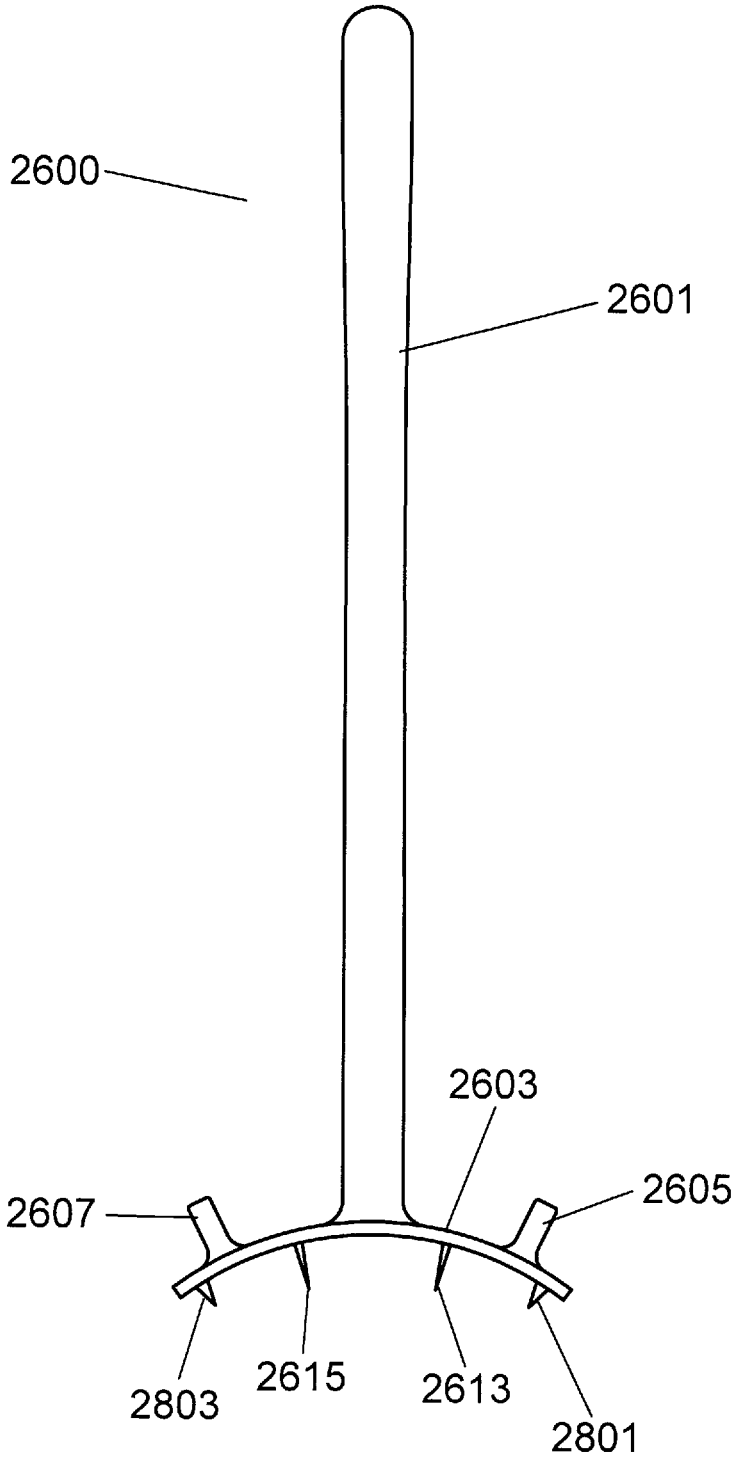
Figure 29:
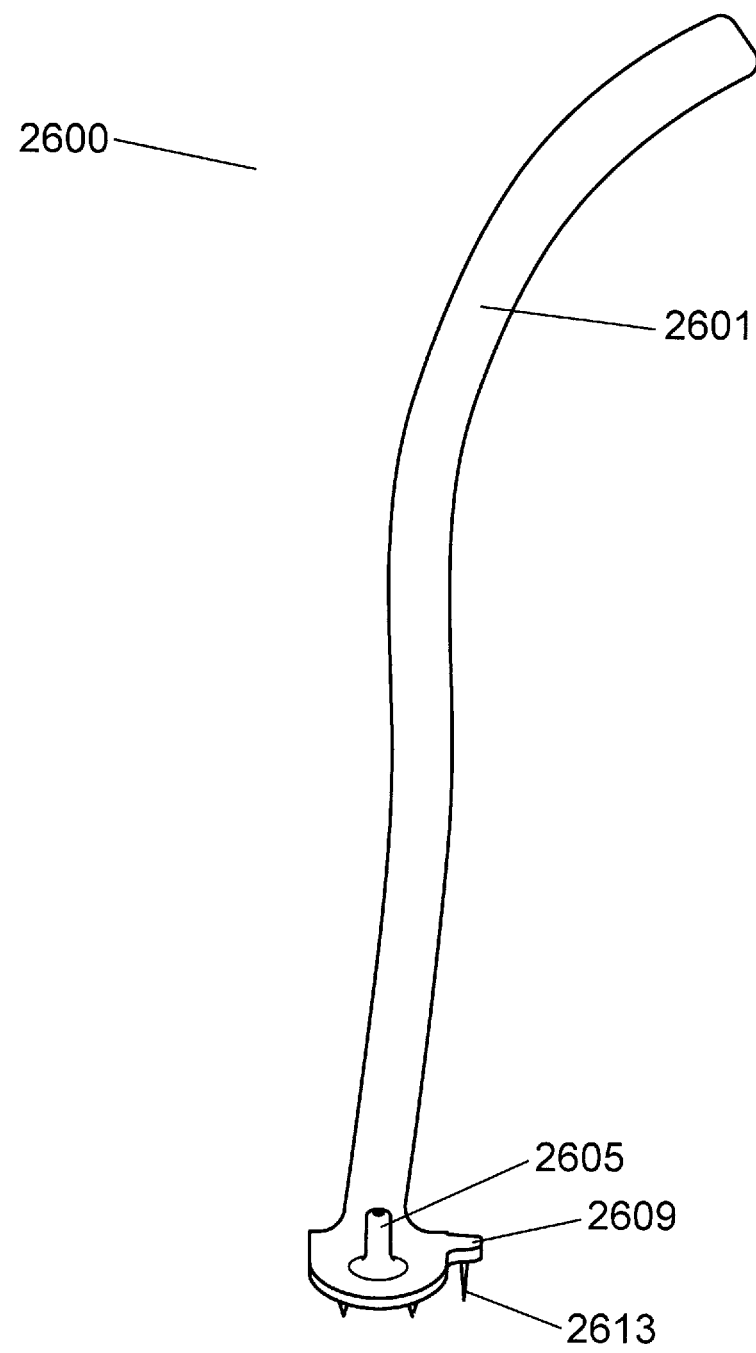
Figure 30:
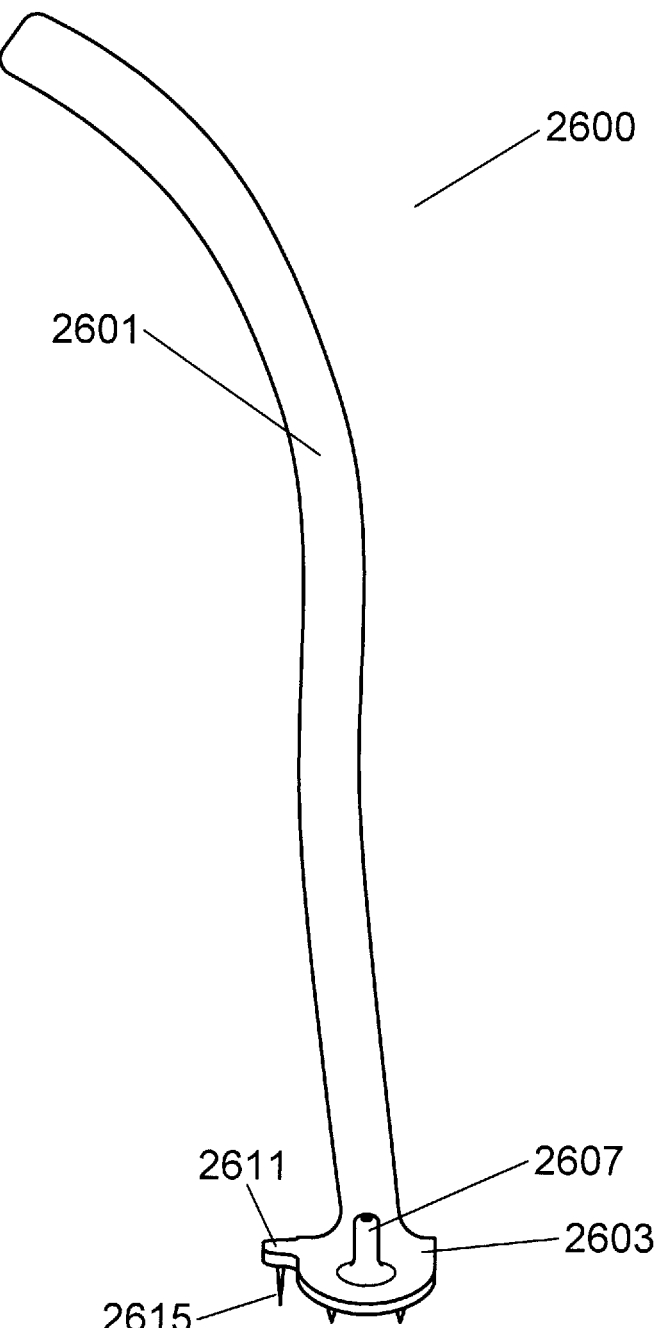
Figure 31:
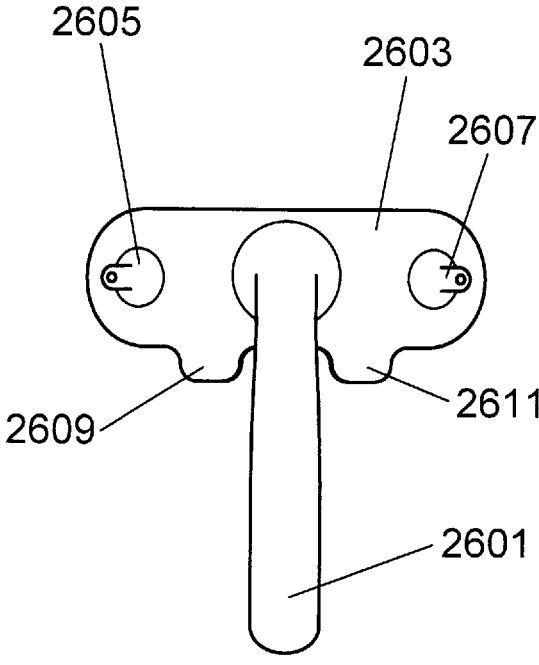

FIG. 17 is a first attachment end perspective view of the tendon repair implant of FIG. 10;

FIG. 18 is a second attachment end perspective view of the tendon repair implant of FIG. 10;

FIG. 19 is a perspective view of a surgical retainer for the tendon repair implant of the present invention;

FIG. 20 is a side plan view of the surgical retainer of FIG. 19;

FIG. 21 is an alternate side plan view of the surgical retainer of FIG. 19;

FIG. 22 is a rotated side plan view of the surgical retainer of FIG. 19;

FIG. 23 is an alternate rotated side plan view of the surgical retainer of FIG. 19;

FIG. 24 is a top perspective view of the surgical retainer of FIG. 19;

FIG. 25 is a bottom perspective view of the surgical retainer of FIG. 19;

FIG. 26 is a perspective view of a drill guide tor the tendon repair implant of the present invention;

FIG. 27 is a side plan view of the drill guide of FIG. 26;

FIG. 28 is an alternate side plan view of the drill guide of FIG. 26;

FIG. 29 is a rotated side plan view of the drill guide of FIG. 26;

FIG. 30 is an alternate rotated side plan view of the drill guide of FIG. 26;

FIG. 31 is a top perspective view of the drill guide of FIG. 26; and

Figure 32:
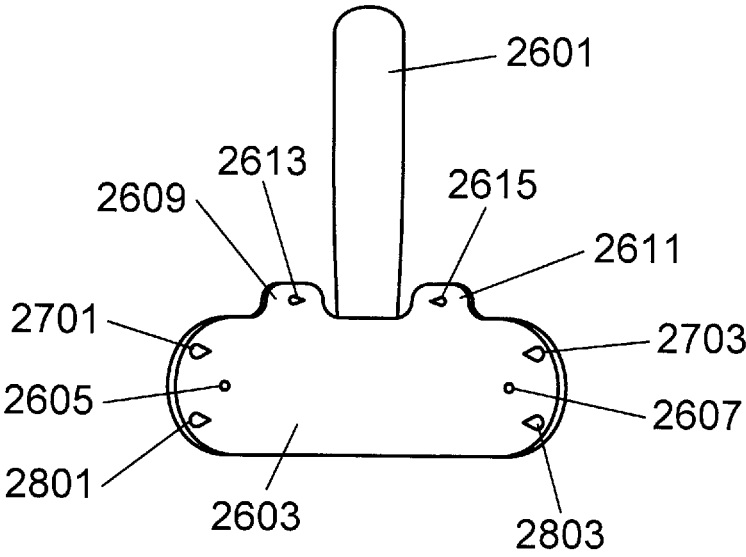

FIG. 32 is a bottom perspective view of the drill guide of FIG. 26.

The present invention will be described in connection with a preferred embodiment, however, it will be understood that there is no intent to limit the invention to the embodiment described. On the contrary, the intent is to cover all alternatives, modifications, and equivalents as may be included within the spirit and scope of the invention as defined by this specification, claims and drawings attached hereto.

BEST MODE FOR CARRYING OUT THE INVENTION

A Tendon Repair Implant and related surgical instruments are described herein. The Tendon Repair Implant provides a more uniform and less bulky repair site, with improved retention and strength of repair. Further, the Tendon Repair Implant does not require immobilization, reducing the possibility of permanent stiffness and related complications.

Figure 1:
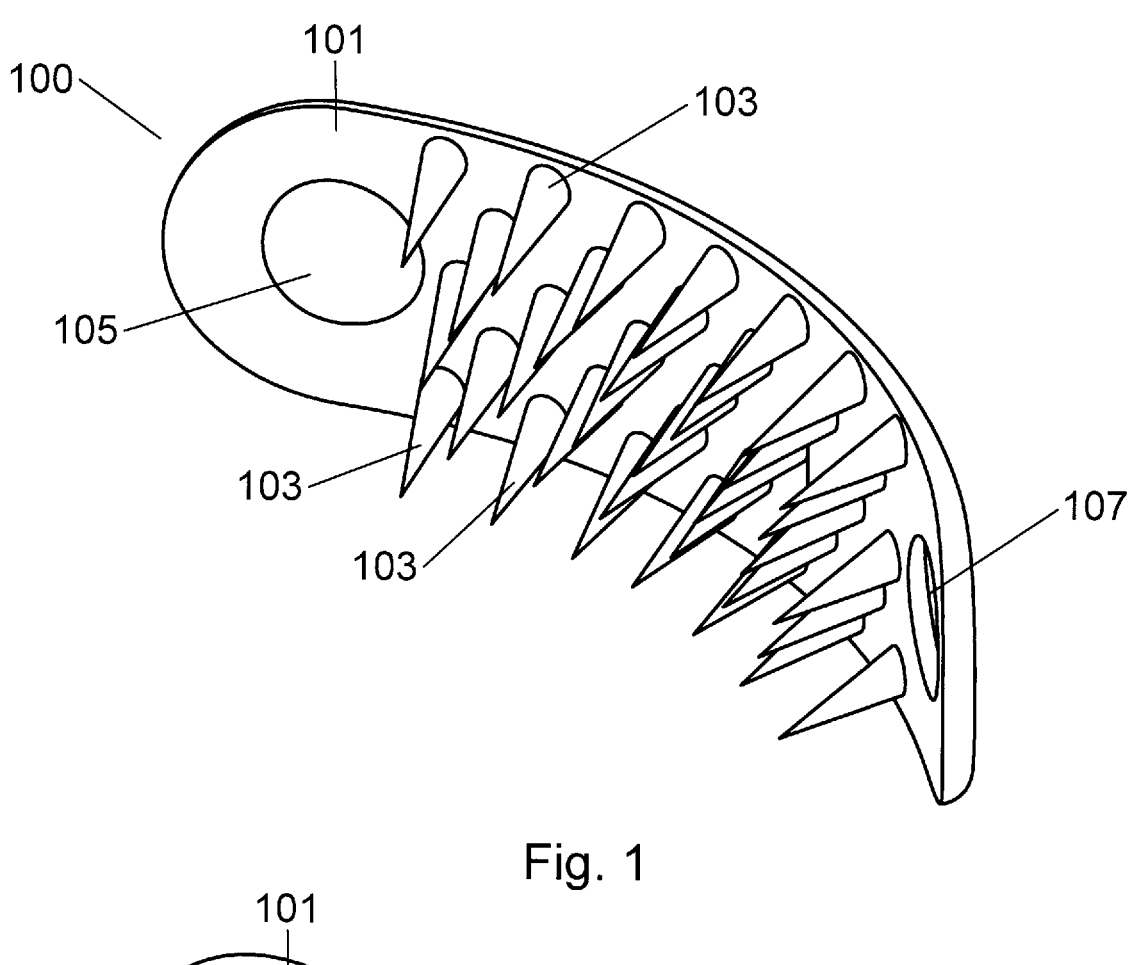
FIG. 1 depicts a perspective view of the tendon repair implant.

Turning first to FIG. 1, a perspective view of the Tendon Repair Implant 100 can be seen. The tendon repair implant 100 is made from a biocompatible material such as a stainless steel or similar metal, or a plastic. In some embodiments, the tendon repair implant 100 may be made from a biodegradable or biomimetic material. The tendon repair implant 100 has an elongated substrate 101 with a convex side and a concave side or other such geometry to facilitate placement on an anatomical structure such as a bone. The substrate 101 has a plurality of spikes 103 protruding from the concave side. The spikes 103 serve to hold a tendon to a bone without the risk of the tendon slipping out from the substrate 101. As will be more fully appreciated after a complete review of this specification, the tendon repair implant is fastened to a bone with the tendon under repair being frictionally engaged between the tendon repair implant and the bone, where the tendon repair implant is retained to the bone by way of screws, anchors, or the like. Each spike protrudes from the concave side of the substrate at an angle in the range of zero degrees to 45 degrees with respect to a line perpendicular to the concave surface of the substrate where the spike originates. In a preferred embodiment of the present invention, the angle of each spike is approximately 20 degrees with respect to a line perpendicular to the concave surface of the substrate where the spike originates. In an exemplary embodiment, each spike 103 is approximately 1 millimeter in length. In some embodiments of the present invention, the spikes 103 are coated or otherwise deposited with a drug eluting material or layer.

The substrate 101 has a first attachment 105 for fastening the substrate 101 to a mammalian bone with the concave side of the substrate 101 facing the mammalian bone, and a second attachment 107 for fastening the substrate 101 to a mammalian bone with the concave side of the substrate 101 facing the mammalian bone. Each attachment may be, for example, a hole for placement of a bone attachment or bone fixation device, or may include an anchor, retainer, or the like. The holes, for example, are capable of receiving a surgical screw, and may, in some embodiments, have a tapered perimeter for securing a surgical screw.

The substrate 101 may, for example, have a rectangular form, and in some embodiments of the present invention, each corner of this rectangular substrate has a radius or is rounded or otherwise curved. The elongated substrate 101 may, in some embodiments of the present invention, be in the range of 9 to 16 millimeters in length.

Figure 2:
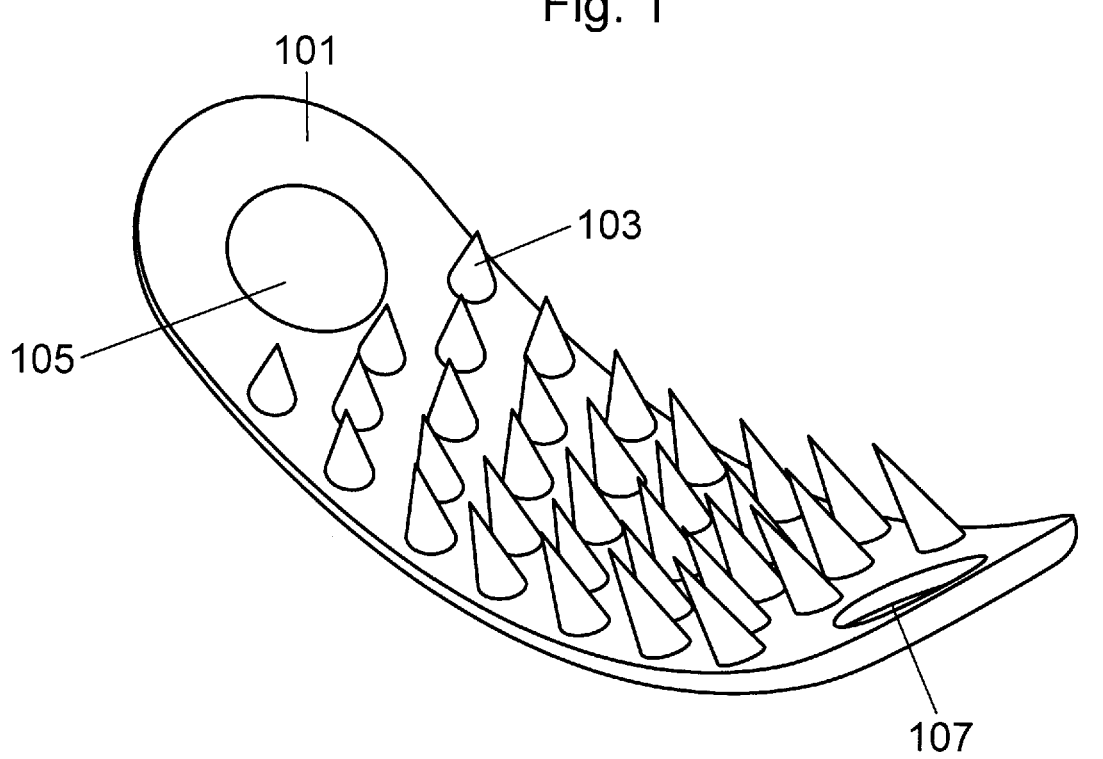
FIG. 2 is a further perspective view of the tendon repair implant.

FIG. 2 is a further perspective view of the tendon repair implant that shows the concave side with spikes 103. The spikes 103 can be seen protruding from the substrate 101 at an angle. The spikes may be conically tapered, or may be pins or other such protrusions that are sufficient to grasp and retain a tendon. The spikes 103 may also be of a uniform diameter with a point, barb, or the like.

Figure 3:
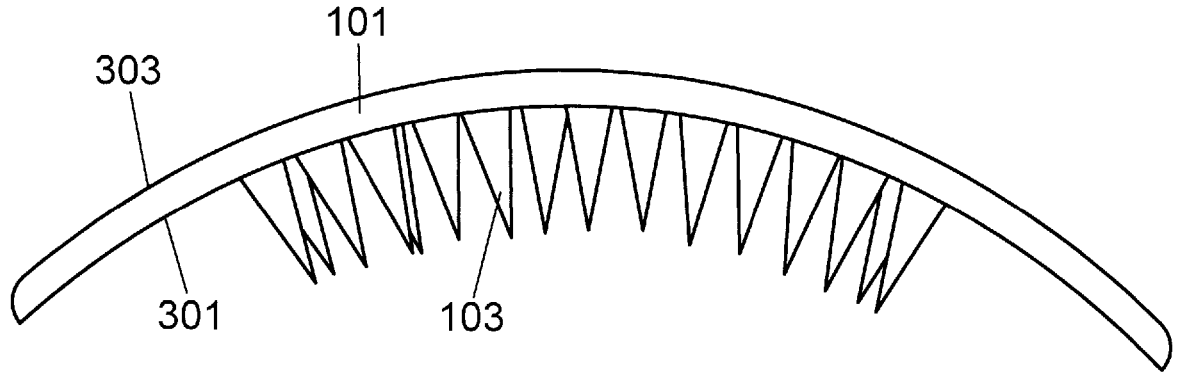
FIG. 3 is a profile view of the tendon repair implant.

FIG. 3 is a profile view of the tendon repair implant w here the concave side 301 and the convex side 303 can be clearly seen along with the plurality of spikes 103. The concave side 301 of the substrate in some embodiments conforms to the phalanges of a patient, or the substrate 101 and related spikes may be malleable or otherwise deformable to accommodate various bone shapes and forms. In some embodiments, a surgical retainer such as the surgical retainer 1900 described herein provides the ability to shape or form the tendon repair implant during surgical placement.

Figure 4:
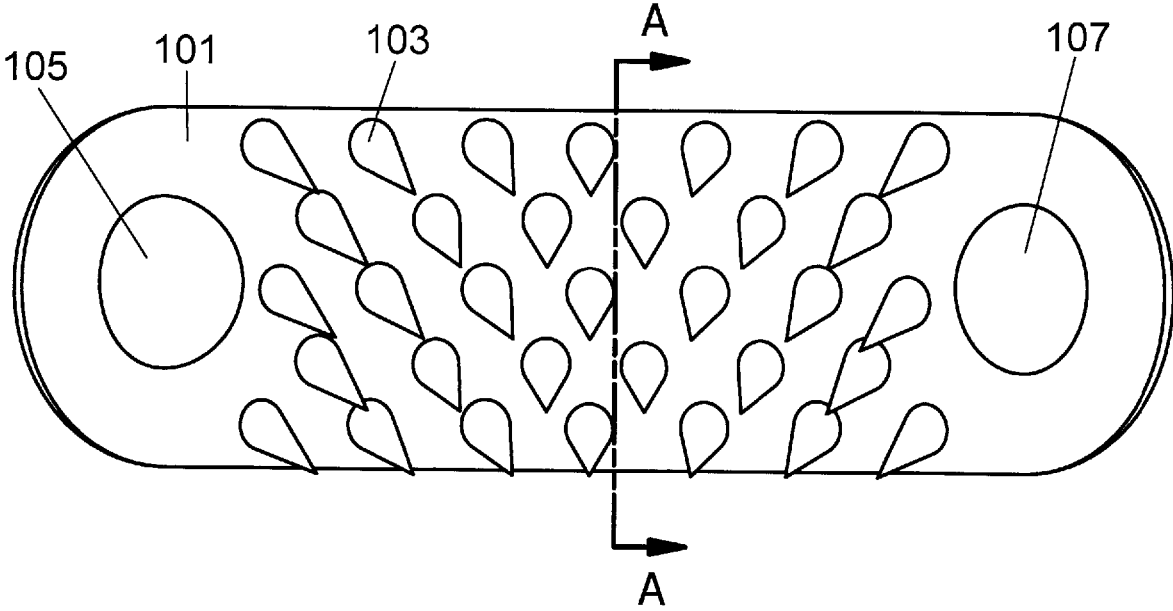
FIG. 4 is a concave side plan view of the tendon repair implant.

FIG. 4 is a concave side plan view of the tendon repair implant 100 showing the spikes 103 protruding outwardly.

Figure 5:
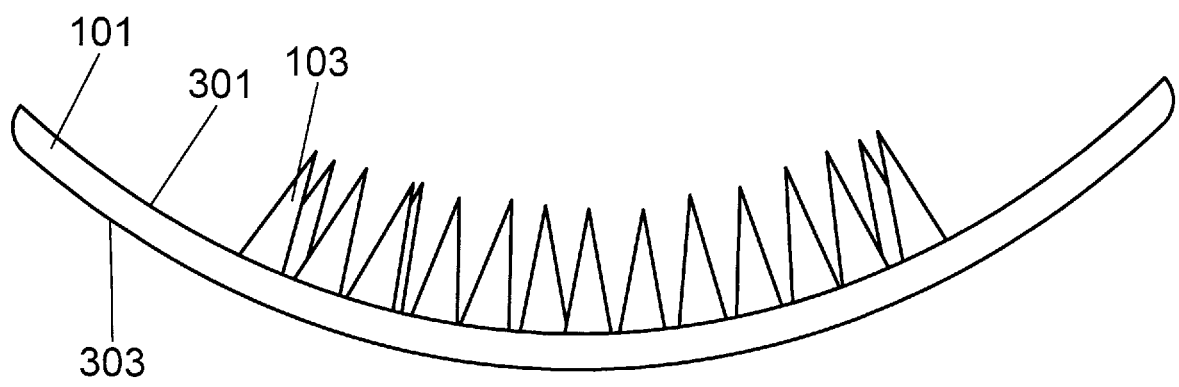
FIG. 5 is an alternate profile view of the tendon repair implant.

FIG. 5 is an alternate profile view of the tendon repair implant showing the concave side 301 and the convex side 303 of the substrate 101.

Figure 6:
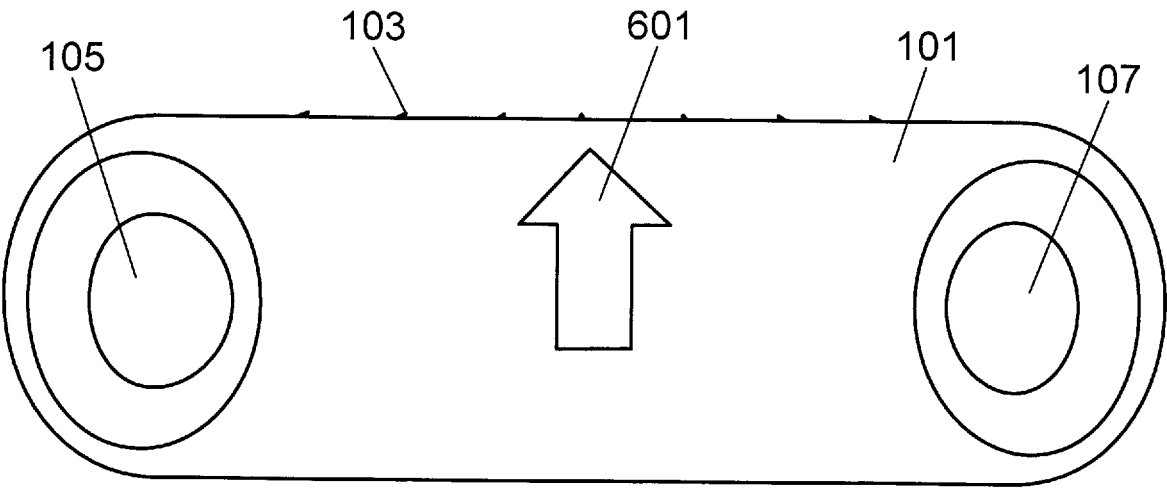
FIG. 6 is a convex side view of the tendon repair implant.

FIG. 6 is a convex side view of the tendon repair implant where a directional indicator 601 such as an arrow or similar symbol can be seen. The directional indicator 601 provides the surgeon with the proper orientation of the tendon repair implant 100 such that the angled spikes 103 properly and adequately grasp the tendon being repaired and affixed to the bone. The directional indicator 601 may be formed with the substrate, etched or engraved on the substrate, or the like.

FIG. 7 is a cross sectional view of the tendon repair implant taken along line A-A of FIG. 4. The angle 701 of each spike can be seen clearly in FIG. 7, and is shown as an example, and not a limitation. Other angles may also be employed as described herein. Further, barbs, hooks, cleats or other retainers may be employed to facilitate tendon attachment.

FIG. 8 is a first attachment 105 end perspective view of the tendon repair implant 100 and FIG. 9 is a second attachment 107 end perspective view of the tendon repair implant 100.

The tendon repair implant 100 thus comprises an elongated substrate comprising a convex side and a concave side; a plurality of spikes protruding from the concave side; wherein each spike protrudes from the concave side of the substrate at an angle in the range of zero degrees to 45 degrees with respect to a line perpendicular to the concave surface of the substrate where the spike originates; a first attachment for fastening the substrate to a mammalian bone with the concave side of the substrate facing the mammalian bone; and a second attachment for fastening the substrate to a mammalian bone with the concave side of the substrate facing the mammalian bone.

In some embodiments of the tendon repair implant, the first attachment and the second attachment are holes capable of receiving a surgical screw. The holes, in some embodiments, may have a tapered or angled perimeter for securing a surgical screw.

In some embodiments of the tendon repair implant, the substrate has a rectangular form with each corner of the rectangle having a radius.

In some embodiments of the tendon repair implant, the tendon repair implant may further comprise a directional indicator that provides a visual indication of proper orientation of the tendon repair implant during surgery.

In some embodiments of the tendon repair implant, the angle of each spike is 20 degrees with respect to a line perpendicular to the concave surface of the substrate where the spike originates.

In some embodiments of the tendon repair implant, each spike is 1 millimeter in length.

In some embodiments of the tendon repair implant, the elongated substrate is in the range of 9 millimeters to 16 millimeters in length.

In some embodiments of the tendon repair implant, the concave surface of the substrate conforms to a phalanges of a patient.

In some embodiments of the tendon repair implant, the tendon repair implant further comprises a drug eluting coaling deposited on the spikes.

FIG. 10 depicts a perspective view of the tendon repair implant with attached bone attachment devices where the tendon repair implant 1000 has a substrate 1001 with spikes 1003 protruding outwardly. Fitted to each attachment is a bone attachment device. FIG. 10 depicts a first bone attachment device 1005 and a second bone attachment device 1007. In one embodiment of the present invention, the bone attachment devices each comprise an expandable flange joined with a hole in the substrate 1001 where the hole allows for placement and entry of a surgical screw into the expandable flange of the bone attachment device. In some embodiments of the present invention, the expandable flange of each bone attachment device is segmented to allow for expansion of the flange when a surgical screw is entered into the expandable flange. The bone attachment devices may be attached to the tendon repair implant 100, or may be integral or formed with the tendon repair implant 1000.

Figure 11:
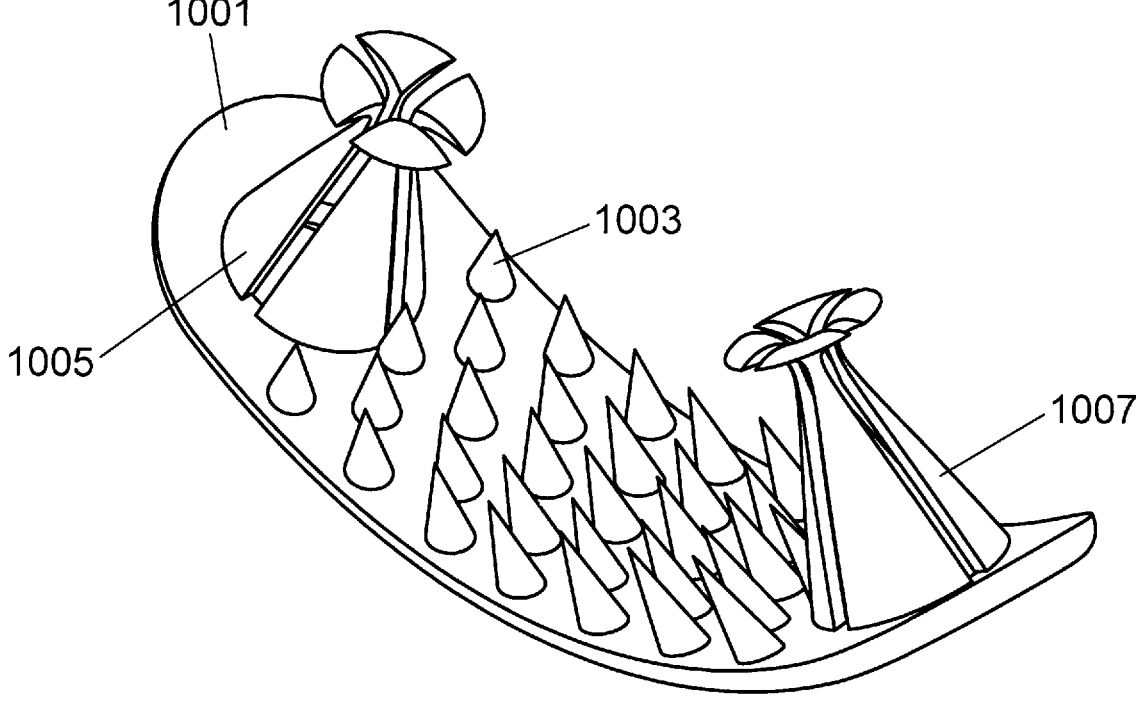
FIG. 11 is a further perspective view of the tendon repair implant of FIG. 10.

FIG. 11 is a further perspective view of the tendon repair implant of FIG. 10 that more clearly shows the structure of the implant.

Figure 12:
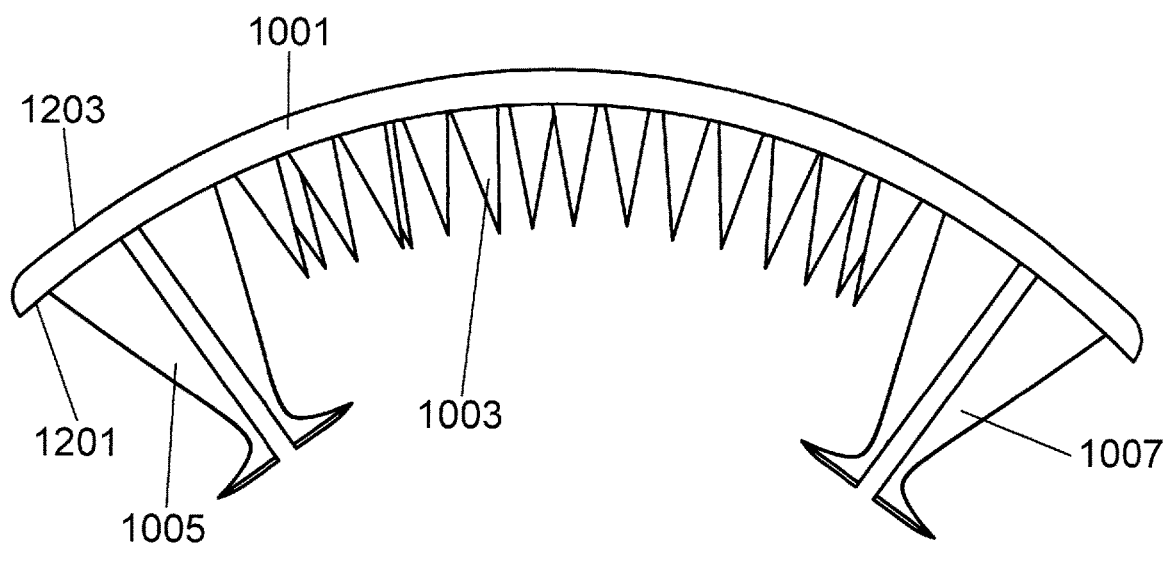
FIG. 12 is a profile view of the tendon repair implant of FIG. 10.

FIG. 12 is a profile view of the tendon repair implant of FIG. 10 where the concave side 1201 and the convex side 1203 can be seen.

Figure 13:
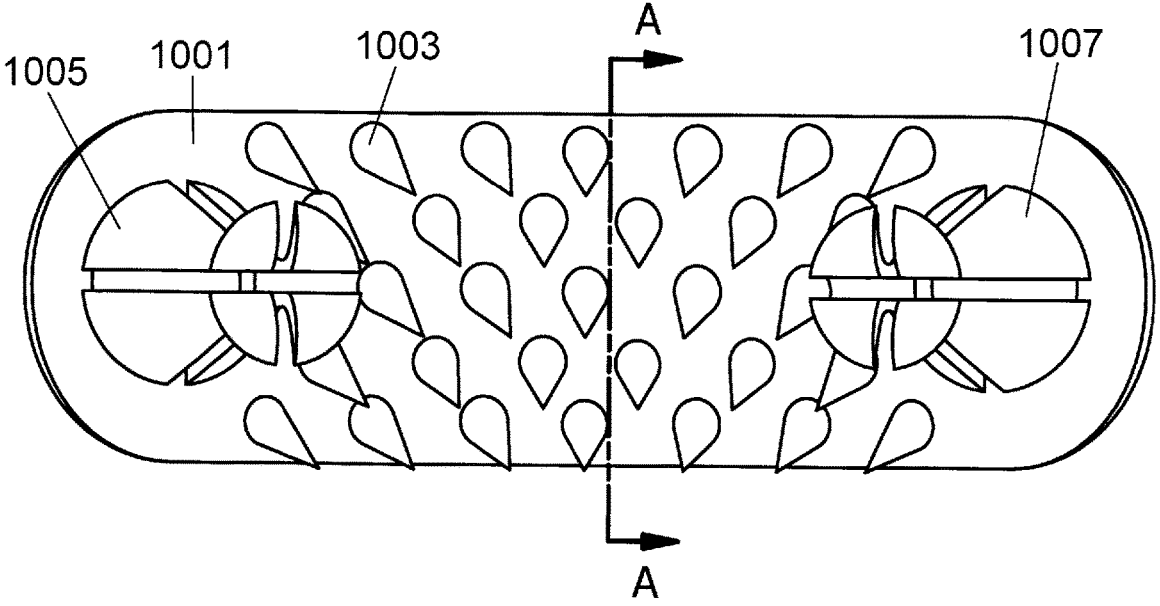
FIG. 13 is a concave side plan view of the tendon repair implant of FIG. 10.
Figure 14:
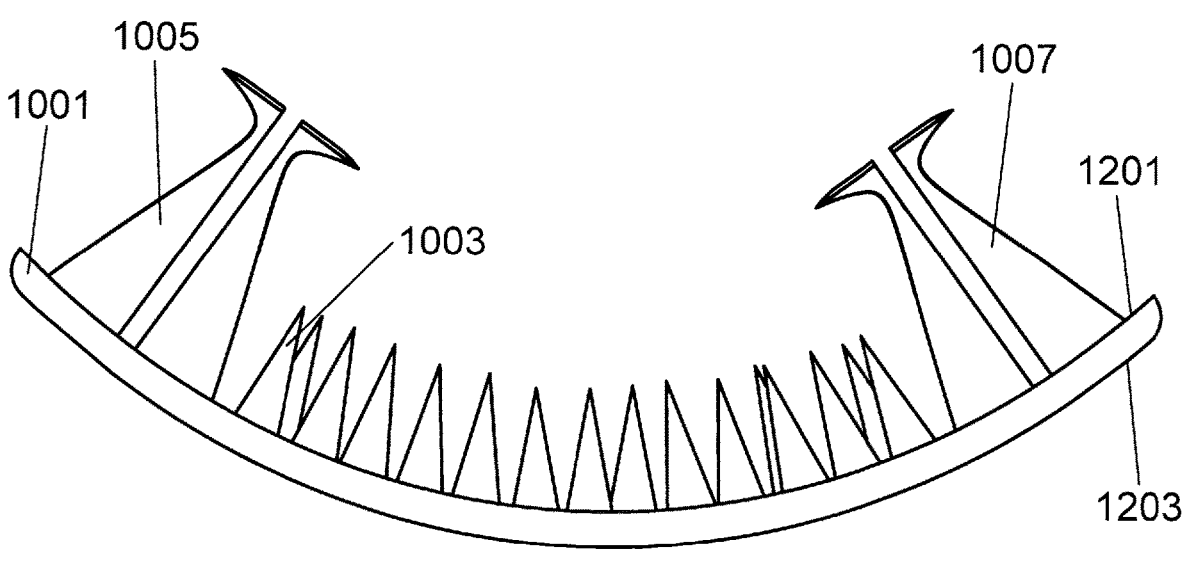
FIG. 14 is an alternate profile view of the tendon repair implant of FIG. 10.

FIG. 13 is a concave side plan view of the tendon repair implant of FIG. 10 and FIG. 14 is an alternate profile view of the tendon repair implant of FIG. 10.

Figure 15:
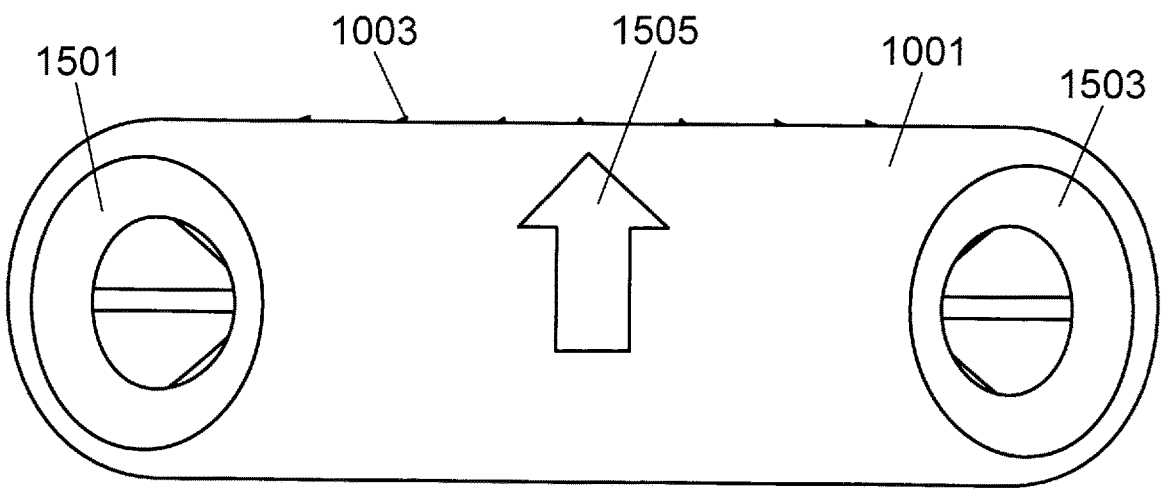
FIG. 15 is a convex side view of the tendon repair implant of FIG. 10.

FIG. 15 is a convex side view of the tendon repair implant of FIG. 10 where the first attachment opening 1501 and the second attachment opening 1503 can be seen. A directional indicator 1505 such as an arrow or other symbol can also be seen to indicate to the surgeon the proper orientation of the tendon repair implant when being implanted in a patient.

Figure 16:
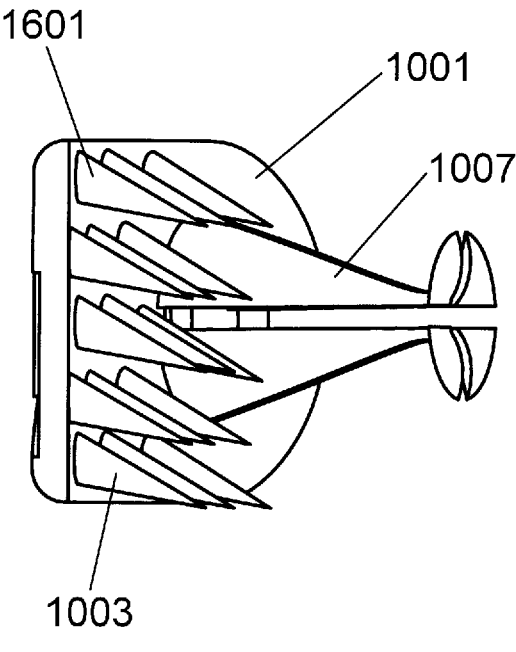
FIG. 16 is a cross sectional view of the tendon repair implant of FIG. 10 taken along line A-A of FIG. 13.

FIG. 16 is a cross sectional view of the tendon repair implant of FIG. 10 taken along line A-A of FIG. 13. The angle 1601 of the spikes 1003 can be clearly seen.

FIG. 17 is a first attachment 1501 end perspective view of the tendon repair implant of FIG. 10 and FIG. 18 is a second attachment 1503 end perspective view of the tendon repair implant of FIG. 10.

FIGS. 10-17 thus depict a tendon repair implant in accordance with the present invention where the tendon repair implant comprises an elongated substrate comprising a convex side and a concave side; a plurality of spikes protruding from the concave side; wherein each spike protrudes from the concave side of the substrate at an angle in the range of zero degrees to 45 degrees with respect to a line perpendicular to the concave surface of the substrate where the spike originates; a first bone attachment device for fastening the substrate to a mammalian bone with the concave side of the substrate facing the mammalian bone; and a second bone attachment device for fastening the substrate to a mammalian bone with the concave side of the substrate facing the mammalian bone.

In some embodiments of the tendon repair implant, the first bone attachment device and the second bone attachment device each comprise an expandable flange joined with a hole in the substrate where the hole allows for placement and entry of a surgical screw into the expandable flange of the bone attachment device.

In some embodiments of the tendon repair implant, the expandable flange of each bone attachment device is segmented to allow for expansion of the flange when a surgical screw is entered into the expandable flange.

In some embodiments of the tendon repair implant, the substrate has a rectangular form with each corner of the rectangle having a radius.

In some embodiments of the tendon repair implant, the tendon repair implant further comprises a directional indicator that provides a visual indication of proper orientation of the tendon repair implant during surgery.

In some embodiments of the tendon repair implant, the angle of each spike is 20 degrees with respect to a line perpendicular to the concave surface of the substrate where the spike originates.

In some embodiments of the tendon repair implant, each spike is 1 millimeter in length.

In some embodiments of the tendon repair implant, the elongated substrate is in the range of 9 millimeters to 16 millimeters in length.

In some embodiments of the tendon repair implant, the concave surface of the substrate conforms to a phalanges of a patient.

In some embodiments of the tendon repair implant, the tendon repair implant further comprises a drug eluting coating deposited on the spikes.

The tendon repair implant of the present invention requires not only skilled and precise placement, but also accurate placement of drill holes in the bone prior to implantation and securing. Surgical instruments to assist in the process of drilling, placement and securing are extremely advantageous as they minimize surgical time, allow for a smaller incision, and reduce trauma of the surgical area by providing efficient and accurate implantation with minimal movement of the implant, surgical tools and related surgical devices.

What is therefore needed and highly desirable is both a drill guide instrument for accurate placement of drilled holes in the bone, and also a surgical retainer for efficient and accurate retention, placement, and release of the tendon repair implant during surgery. Both of these instruments wilt be further described herein by way of the following detailed description and accompanying drawings. As would be expected, both of the surgical instruments are manufactured from a surgically acceptable material such as a stainless steel, titanium, or other surgically acceptable metal or plastic. The surgical instruments may be made by machining, casting, 3D printing, or the like.

It should be noted that the surgical retainer may, in some embodiments, contain a pre-loaded or otherwise attached or retained tendon repair implant. This allows not only for surgical convenience, but reduces errors in areas such as implant sizing, orientation, and the like. The surgical retainer and tendon repair implant may, in some instances, be considered as one item. In some embodiments of the present invention, the surgical retainer is sized along with the tendon repair implant so that the two properly couple and work together as one.

A surgical retainer for the tendon repair implant disclosed herein will be described by way of FIGS. 19-25.

Turning now to FIG. 19, a perspective view of a surgical retainer 1900 for the tendon repair implant of the present invention is depicted. The surgical retainer comprises an implant backer 1903 of a shape similar to that of the tendon repair implant to allow for close retention of the tendon repair implant by the implant backer 1903. The implant backer has a concave side and a convex side where the concave side is configured to receive a tendon repair implant. The implant backer has retention prongs that releasably grasp a tendon repair implant that is being placed during surgery. The retention prongs are curled or formed such that they grasp a tendon repair implant, but have some flexibility to allow for the tendon repair implant 10 to be retained and also removed without difficulty. A first retention prong 1909 and a second retention prong 1911 can be seen in FIG. 19 along with a third retention prong 1913 and a fourth retention prong 1915. Two retention prongs may be adequate for retention and release of the tendon repair implant, however, in some embodiments of the present invention four or even six or more retention prongs may be employed. To facilitate placement of a bone screw or similar anchor with the surgical retainer 1900 still grasping the tendon repair implant, a first bone screw cutout 1905 and a second bone screw cutout 1907 are formed with the implant backer. Each bone screw cutout may be generally U-shaped or generally V-shaped, with distal ends or corners forming or otherwise comprising retention prongs. A handle 1901 is also attached to the implant backer 1903 for surgical control and placement of the retained tendon repair implant. A curve can also be seen in the handle 1901 to allow for efficient and precise control of the surgical retainer 1900. A sutures cleat 1917 can also be seen affixed or otherwise formed with the handle 1901. In some embodiments of the present invention, the sutures cleat 1917 has a wedge for temporary frictional engagement and retention of a suture.

A fifth retention prong 2001 and a sixth retention prong 2003 may also be employed along an elongate edge of the implant backer 1903, as seen in the side plan view of the surgical retainer depicted in FIG. 20.

FIG. 21 is an alternate side plan view of the surgical retainer of FIG. 19 that also depicts the fifth retention prong 2001 and the sixth retention prong 2003 between the second retention prong 1911 and the third retention prong 1913.

FIG. 22 is a rotated side plan view of the surgical retainer of FIG. 19 that clearly shows the curvature of the handle 1901. In some embodiments of the present invention, the curvature may depart from that depicted, or the curvature may be absent altogether.

FIG. 23 is an alternate rotated side plan view of the surgical retainer of FIG. 19 that also shows the placement of the sutures cleat 1917. The curled under form of the retention prongs can also be seen clearly.

FIG. 24 is a top perspective view of the surgical retainer of FIG. 19. To also depict the placement of all six retention prongs (when so employed), FIG. 25 is a bottom perspective view of the surgical retainer of FIG. 19.

FIGS. 19-25 thus depict a surgical retainer for a tendon repair implant in accordance with the present invention that comprises an implant backer having a first retention prong and a second retention prong; a first bone screw cutout and a second bone screw cutout formed with the implant backer; a handle attached to the implant backer; wherein the implant backer has a concave side and a convex side where the concave side is configured to receive a tendon repair implant; and wherein the first retention prong and the second retention prong are configured to releasably grasp a tendon repair implant.

In some embodiments, the surgical retainer further comprises a third retention prong and a fourth retention prong attached to the implant backer.

In some embodiments, the surgical retainer further comprises a sutures cleat affixed to the handle. The sutures cleat may also have a feature or geometry such as a wedge for temporary frictional engagement and retention of a suture.

In some embodiments, the surgical retainer further comprises a fifth retention prong and a sixth retention prong attached to the implant backer.

While the surgical retainer 1900 has been heretofore described, a drill guide instrument for the tendon repair implant may be used in surgery prior to the use of the surgical retainer. The drill guide instrument 2600 will now be described and depicted by way of FIGS. 26-32.

FIG. 26 is a perspective view of a drill guide instrument 2600 for the tendon repair implant of the present invention. A drill guide backer 2603 can be seen that conforms to the shape of the tendon repair implant and provides for proper alignment of the first drill guide 2605 and the second drill guide 2607 when the drill guide instrument 2600 is placed in position for subsequent surgical bone drilling prior to implantation of the tendon repair implant. The drill guide backer 2603 has a concave side and a convex side with the first drill guide 2605 and the second drill guide 2607 there through. While the drill guide instrument 2600 is placed by the surgeon, proper alignment on the bone is essential. To accomplish that goal, a first tab 2600 protruding from the drill guide hacker 2603 and a second tab 2611 protruding from the drill guide backer 2603 both have an alignment pin extending downward from each tab. The first alignment pin 2613 and the second alignment pin 2615 extend down from their respective tab and engage between finger bones during surgery. The pins may be in the range of 1-10 mm long, with 5 mm being a preferred length. A handle 2601 can also be seen affixed to the drill guide backer 2603. In some embodiments of the present invention the handle 2601 is curved or otherwise tapered or angled.

FIG. 27 is a side plan view of the drill guide instrument of FIG. 26. While the first drill guide 2605 and the second drill guide 2607 are generally perpendicular to the drill guide backer 2603, it is essential to account for the thickness of the tendon repair implant when drilling into the bone for fastening of the tendon repair implant. To allow for this thickness, spacer spikes or protrusions are employed. In FIG. 27, a first spacer spike 2701 and a second spacer spike 2703 can be seen. Various shapes and quantities of spacers may be employed.

FIG. 28 is an alternate side plan view of the drill guide instrument of FIG. 26. In this figure, a third spacer spike 2801 and a fourth spacer spike 2803 can be seen.

FIG. 29 is a rotated side plan view of the drill guide instrument of FIG. 26 and FIG. 30 is an alternate rotated side plan view of the drill guide instrument of FIG. 26. The curvature of the handle 2601 can be clearly seen as well as the protruding tabs 2609 and 2611 and their associated alignment pins 2613 and 2615.

FIG. 31 is a top perspective view of the drill guide instrument of FIG. 26 that shows the first drill guide 2605 and the second drill guide 2607 affixed through the drill guide backer 2603. In one exemplary embodiment of the present invention, the inside diameter of the drill guides is 1.1 millimeter to accommodate a 1.0 millimeter drill bit.

Lastly, FIG. 32 is a bottom perspective view of the drill guide instrument of FIG. 26 that shows the spacer spikes 2701 and 2703 as well as the spacer spikes 2801 and 2803. The first alignment pin 2613 and the second alignment pin 2615 can also be seen protruding from the tabs 2609 and 2611.

FIGS. 26-32 thus depict a drill guide instrument for a tendon repair implant in accordance with the present invention that comprises a drill guide hacker having a concave side and a convex side; a first drill guide and a second drill guide attached through the drill guide backer; the drill guide backer having a concave side, a convex side, a first tab and a second tab; a first alignment pin protruding downward from the first tab; a second alignment pin protruding downward from the second tab; and a handle attached to the drill guide backer.

In some embodiments, the drill guide instrument further comprises a spacer spike protruding from the drill guide backer.

To use the drill guide instrument 2600, the drill guide backer is placed on the subject bone with the alignment pins engaging between linger bones during surgery. Once the drill guide instrument is placed in the proper location and orientation to facilitate tendon repair and reattachment, a suitable drill bit is inserted through each drill guide and a sufficiently deep hole is drilled in the bone. Thus, two holes are drilled to accommodate surgical screws that will be adequate to anchor the tendon repair implant through each attachment.

Once the anchor holes are drilled, a tendon repair implant is positioned through the incision and properly oriented such that the anchor holes align with the attachment holes or features of the tendon repair implant, and the tendon to be repaired is also placed between the tendon repair implant and the bone for retention and secure fastening. Bone screws or anchors are then placed through the first attachment and the second attachment of the tendon repair implant, and the tendon repair implant is then fixed onto the bone such that the tendon is held through the spikes of the tendon repair implant and the attachment of the tendon repair implant to the bone. Surgical procedures continue and the repair is then completed using known surgical techniques and procedures.

It is, therefore, apparent that there has been provided, in accordance with the various objects of the present invention, a Tendon Repair Implant as well as surgical instruments for tendon repair using the Tendon Repair Implant.

While the various objects of this invention have been described in conjunction with preferred embodiments thereof, it is evident that many alternatives, modifications, and variations will be apparent to those skilled in the art. Accordingly, it is intended to embrace all such alternatives, modifications and variations that fall within the spirit and broad scope of this specification, claims and drawings appended herein.

What is claimed is:

1. A tendon repair implant comprising:
an elongated substrate comprising a convex side and a concave side;
a plurality of spikes protruding from the concave side;
wherein each spike protrudes from the concave side of the substrate at an angle in the range of zero degrees to 45 degrees with respect to a line perpendicular to the concave surface of the substrate where the spike originates;
a first attachment for fastening the substrate to a mammalian bone with the concave side of the substrate facing the mammalian bone;
a second attachment for fastening the substrate to a mammalian bone with the concave side of the substrate facing the mammalian bone,
wherein the first attachment comprises a first expandable flange structure joined with a first hole in the elongate substrate, and the second attachment comprises a second expandable flange structure joined with a second hole in the elongate substrate, the first and second expandable flange structures each comprising a base end at the concave side, only a singular flange defining a terminal flanged end, a tapered sleeve body extending fully between the base end at the concave side and the terminal flanged end that narrows as it extends from the base end to the terminal flanged end in an unexpanded state of the respective first or second expandable flange structure, and one or more slots extending from the base end through the tapered sleeve body and the terminal flanged end, the base end of the first expandable flange structure mechanically coupled to, or integral with, a first portion of the elongated substrate, and the base end of the second expandable flange structure mechanically coupled to, or integral with, a second portion of the elongated substrate; and
wherein each spike of the plurality of spikes is positioned between the first attachment and the second attachment.

2. The tendon repair implant of claim 1, wherein the first and second holes have a tapered perimeter for securing a surgical screw.

3. The tendon repair implant of claim 1, wherein the substrate has a rectangular form with each corner of the rectangle having a radius.

4. The tendon repair implant of claim 1, further comprising a directional indicator that provides a visual indication of proper orientation of the tendon repair implant during surgery.

5. The tendon repair implant of claim 1, wherein the angle of each spike is 20 degrees with respect to a line perpendicular to the concave surface of the substrate where the spike originates.

6. The tendon repair implant of claim 1, wherein each spike is 1 millimeter in length, and the elongated substrate is in the range of 9 millimeters to 16 millimeters in length.

7. The tendon repair implant of claim 1, wherein the concave surface of the substrate is configured to conform to a phalange of a patient.

8. The tendon repair implant of claim 1, further comprising a drug eluting coating deposited on the spikes.

9. The tendon repair implant of claim 1, wherein the first expandable flange structure and the first hole allows for placement and entry of a first surgical screw into the first expandable flange structure of the first bone attachment device to expand the first expandable flange structure, and wherein the second expandable flange structure and the second hole allows for placement and entry of a second surgical screw into the second expandable flange structure of the second bone attachment device to expand the first expandable flange structure.

10. The tendon repair implant of claim 1, further comprising a surgical retainer, wherein the surgical retainer comprises:

an implant backer having a first retention prong and a second retention prong;

a first bone screw cutout and a second bone screw cutout formed with the implant backer;

a handle attached to the implant backer;

wherein the implant backer has a concave side and a convex side where the concave side is configured to receive the tendon repair implant; and wherein the first retention prong and the second retention prong are configured to releasably grasp the tendon repair implant.

11. The tendon repair implant of claim 10, wherein the surgical retainer further includes a sutures cleat.

12. The tendon repair implant of claim 1, further comprising a drill guide, the drill guide comprising:

a drill guide backer having a concave side and a convex side;

a first drill guide and a second drill guide attached through the drill guide backer;

the drill guide backer having a concave side, a convex side, a first tab and a second tab; a first alignment pin protruding downward from the first tab;

a second alignment pin protruding downward from the second tab; and a handle attached to the drill guide backer.

13. The tendon repair implant of claim 1, wherein the tapered sleeve body of each of the first and second expandable flange structures defines a smooth outer surface that extends entirely between the terminal flanged end and the concave side of the elongated substrate.

14. The tendon repair implant of claim 1, wherein the one or more slots of each of the first and second expandable flange structures extend fully through the terminal flanged end and the tapered sleeve body such that the one or more slots extend to the concave side of the elongated substrate.

15. The tendon repair implant of claim 1, wherein the elongated substrate, the first expandable flange structure and the second expandable flange form a pre-implantation implant construct.

16. The tendon repair implant of claim 1, wherein the terminal flanged end of each of the first expandable flange structure and the second expandable flange defines a cross-sectional size that is greater than a cross-sectional size of an adjacent portion of the tapered sleeve and that is less than a cross-sectional size of the tapered sleeve at the base end.

17. A tendon repair implant comprising:

an elongated substrate comprising a convex side and a concave side, wherein the convex side of the elongate substrate comprises a directional indicator that provides a visual indication of proper orientation of the tendon repair implant relative to a surgical area;

a plurality of spikes protruding from the concave side;

wherein each spike protrudes from the concave side of the substrate at an angle in the range of zero degrees to 45 degrees with respect to a line perpendicular to the concave surface of the substrate where the spike originates;

a first bone attachment device for fastening the substrate to a mammalian bone with the concave side of the substrate facing the mammalian bone; and a second bone attachment device for fastening the substrate to a mammalian bone with the concave side of the substrate facing the mammalian bone;

wherein the first bone attachment device and the second bone attachment device each comprise an expandable flange structure joined with a hole in the substrate where the hole allows for placement and entry of a surgical screw into the expandable flange structure of the respective bone attachment device; and wherein the expandable flange structure of each bone attachment device comprises only a singular flange defining a terminal flanged end, and a tapered sleeve body extending fully between the concave side of the elongated substrate and the terminal flanged end that narrows as it extends from the concave side to the terminal flanged end in an unexpanded state of the expandable flange structure, and wherein each expandable flange structure is segmented to define one or more channels extending from the concave side of the elongated substrate and through the tapered sleeve body and the terminal flanged end to allow for expansion of the expandable flange structure when a surgical screw is entered into the expandable flange structure.

18. The tendon repair implant of claim 17, wherein the substrate has a rectangular form with each corner of the rectangle having a radius.

19. The tendon repair implant of claim 17, wherein the directional indicator is an arrow indicator.

20. The tendon repair implant of claim 17, wherein the angle of each spike is 20 degrees with respect to a line perpendicular to the concave surface of the substrate where the spike originates.

21. The tendon repair implant of claim 17, wherein each spike is 1 millimeter in length, the elongated substrate is in the range of 9 millimeters to 16 millimeters in length.

22. The tendon repair implant of claim 17, wherein the concave surface of the substrate is configured to conform to a phalange of a patient.

23. The tendon repair implant of claim 17, further comprising a drug eluting coating deposited on the spikes.

* * * * *